(12) United States Patent
Baranov et al.

(10) Patent No.: US 6,399,323 B1
(45) Date of Patent: Jun. 4, 2002

(54) METHOD OF PREPARING POLYPEPTIDES IN A CELL-FREE TRANSLATION SYSTEM

(75) Inventors: Vladimir Ivanovich Baranov; Ljubov Anatolievna Ryabova; Oleg Bronislavovich Yarchuk; Alexandr Sergeevich Spirin, all of Moscow (SU)

(73) Assignee: Institute for Protein Research, Moscow (RU)

( * ) Notice: Subject to any disclaimer, the term of this patent is extended or adjusted under 35 U.S.C. 154(b) by 0 days.

(21) Appl. No.: 07/834,523

(22) PCT Filed: Jun. 14, 1990

(86) PCT No.: PCT/SU90/00151

§ 371 (c)(1),
(2), (4) Date: Mar. 18, 1993

(87) PCT Pub. No.: WO91/02076

PCT Pub. Date: Feb. 21, 1991

(30) Foreign Application Priority Data

Jul. 31, 1989 (SU) .............................. 4717700
May 29, 1990 (SU) ....................... 4823743/13

(51) Int. Cl.$^7$ .......................... C12P 21/06; C07H 21/04
(52) U.S. Cl. ..................... 435/68.1; 435/69.1; 536/23.1
(58) Field of Search .............................. 435/68.1, 69.1, 435/172.3; 536/23.1

(56) References Cited

PUBLICATIONS

Baranov Et Al. (1989), Gene 84: 463–466.*
Krieg Et Al. (1984), Nucl. Acids Res. 12(18):7057–7070.*
Spirin Et Al. (1988), Science 242: 1162–1164.*
Maniatis Et Al. (1982), Molecular Cloning: A Laboratory Manual (Cold Spring Harbor Laboratory Press). pp. 344–349.*
Pratt Et Al. (1981), Nucl. Acids Res. 9(18):4459–4474.*

* cited by examiner

*Primary Examiner*—Terry McKelvey
*Assistant Examiner*—William Sandals
(74) *Attorney, Agent, or Firm*—Arent Fox Kintner Plotkin & Kahn

(57) ABSTRACT

Polypeptides are synthesized in cell-free translation system containing an exogenous RNA-polymerase, DNA molecules as protein genes, nucleic acid and substrates. It contains ATP, GTP, CTP, UTP and amino acids as substrates. During the translation process in the system the following products are synthesized: a specific polypeptide, AMP, GDP, CDP, UDP, pyrophosphate and inorganic phosphate. As the substrates are consumed for the synthesis of the products, the translation products including the specific polypeptide, AMP, GDP, CDP, UDP, pyrophosphate and inorganic phosphate are removed from the system and simultaneously substrates such as ATP, GTP, CTP, UTP and amino acids are delivered to maintain their initial concentration.

10 Claims, 4 Drawing Sheets

2 4 6 8 10

0 0.5 5 7 9 12

METHOD OF PREPARING POLYPEPTIDES IN A CELL-FREE TRANSLATION SYSTEM

FIELD OF THE ART

This invention relates to molecular biology and bioengineering, and more particularly to methods of preparing polypeptides in a cell-free translation system.

Said polypeptides are widely used in medicine as regulators of biological processes. Known in the prior art are, e.g., polypeptides activating the immune system, polypeptides which are neuromediators and transmitters, polypeptides regulating salt metabolism, etc. Polypeptides are also used in agriculture as biological stimulants, e.g., growth hormones. They are also used in bioelectronics, e.g., as rodopsin films.

STATE OF THE ART

Known in the art is a method for a preparative expression of cell genetic material by the method of genetic engineering based on the introduction of a foreign DNA into a live cell, the genetic material of said foreign DNA being expressed by the apparatus of the host cell. This method is widely employed in commercial production of proteins.

However, the method has a limited application. This is associated with the complexity of isolation of the products of gene expression by the transformed cells, lethality of some specific products for the host cell, elimination of the transformed plasmids from the cell, proteolytic degradation or aggregation of the product of expression of the foreign gene.

It follows from the foregoing that the method of genetic engineering does not provide for possibilities of a preparative expression of all genes.

Known is another method of expression of genes based on the use of a cell-free system of continuous conjugated transcription/translation (Gene, 1989, v. 84, p. 463). This system is free of limitations imposed by a cell and ensures expression of substantially any gene in the form of a DNA molecule engineered in the required manner.

However, this method cannot be applied for cell-free eukaryotic systems. The problem is that upon expression of genes by the said method the use is made of endogenous RNA-polymerases of the cells employed for preparation of the cell-free system of conjugated transcription/translation. This requires the use of special methods for isolation of the cell extract which ensure the maintenance of the activity of endogenous RNA-polymerases. Moreover, in eukaryotic cells the transcription and translation processes are, as a rule, dispersed in space and time: the transcription takes place in the cell nucleus, while the translation occurs in the cell cytoplasm after relevant modifications of mRNA. Therefore up to the present all attempts to obtain a reliable system of conjugated transcription/translation based on eukaryotic cell extracts have been unsuccessful. The only method providing a reliable preparation of such extracts is based on the preparation of the S30 extract from bacterial cells of *Escherichia coli*. Besides, the plasmid containing the gene coding for the specific product has a selection gene (a gene providing resistance to the action of an antibiotic) which is also controlled by an promoter of the RNA-polymerase of *E. coli* and is expressed as efficiently as the gene coding for the specific product. As a result, in addition to the specific product, a side product is synthesized upon functioning of the system.

Known in the art is one more method of preparative synthesis of polypeptides based on the use of continuous cell-free translation system containing a template RNA as a nucleic acid. This method consists in preparing polypeptides on ribosomes in a cell free translation system containing ATP, GTP and amino acids as substrates accompanied by the formation of translation products in the system which include the specific product, AMP, GDP, pyrophosphate and inorganic phosphate. In the process of translation, translation products, including AMP, GDP, pyrophosphate, inorganic phosphate and the specific product, are removed from the system as substrates are converted to products with a simultaneous delivery in the system of substrates in the form of amino acids, ATP, GTP to maintain their initial concentration unchanged (Science, 1988, v. 242, p. 1162).

Said method makes it possible to carry out preparative synthesis of substantially any polypeptides in cell-free translation systems prepared from cells of any organisms.

However, the application of this method makes impossible the expression of the genetic material as DNA molecules. A template RNA is used in this method. This means that to realize the method, it is necessary to carry out an additional synthesis of template RNAs. As known, a template RNA is obtained from DNA molecules using transcription by RNA-polymerases. This is a labor-consuming and expensive process. Thus, at present the available methods do not permit to synthesize polypeptides using DNA molecules in any cell-free systems.

DISCLOSURE OF THE INVENTION

The object of the invention is to develop such a method of preparation of polypeptides in cell-free systems which would ensure preparation of polypeptides with the use of DNA molecules in any cell-free system based on both prokaryotic and eukaryotic extracts.

This object is accomplished by provision of the method for preparation of polypeptides in the cell-free translation system containing a nucleic acid and ATP, GTP, and amino acids as substrates, with formation of translation products including the specific polypeptide, AMP, GDP, pyrophosphate and inorganic phosphate which are removed from the system as substrates are consumed with a simultaneous delivery of ATP, GDP and amino acids as substrates for maintenance of their initial concentration. According to the invention, the system also contains an exogenous RNA-polymerase as well as DNA molecules comprising protein-coding genes with promoter sites specific to the above polymerase, CTP and UPD as substrates and, in addition, CDP and UDP as products.

Prokaryotic and eukaryotic cell-free translation systems are used as cell-free translation systems according to the invention. E.g., systems based on *E. coli* extracts can be used as prokaryotic cell-free systems, and systems based on extracts from wheat embryos or on lysates from rabbit reticulocytes can be used as eukaryotic cell-free systems. The ratio of the components in the reaction mixture, ion and temperature conditions of the synthesis are optimal for the organisms from which cell-free systems and exogenous RNA-polymerases are prepared. The range of these conditions is rather wide.

The method implies the use of an exogenous phage RNA-polymerase, e.g., phage T7 RNA-polymerase or phage SP6 RNA-polymerase, as an exogenous RNA-polymerase.

As said, in some cases it is expedient to use a prokaryotic cell-free system based on *E. coli* extracts. Such a translation system contains an endogenous RNA-polymerase. To prevent the formation of additional translation products, an additional delivery of an inhibitor of the endogenous RNA-polymerase should be used. E.g., rifampicin is used as an inhibitor of the prokaryotic endogenous RNA-polymerase.

The nucleic acid employed in the system in represented by the protein-coding in the form of DNA molecules with promoter sites specific to an exogenous RNA-polymerase. Such protein-coding genes can be contained in, DNA molecules obtained by amplification of a DNA fragment or plasmid DNA.

The proposed method has no disadvantages of the genetic engineering method and known methods of preparative synthesis of polypeptides in continuous cell-free translation systems. It provides preparation of polypeptides within various cell-free systems without a preliminary synthesis of template RNA molecules. Due to the choice of the components, the synthesis of a template RNA proceeds directly in the cell-free system.

The proposed method ensures the preparative synthesis of polypeptides at a constant rate during tens of hours with a yield of the functionally active product (polypeptide) of 1 to 10 nmol per 1 ml of the reaction mixture and can be employed in commercial production of preparing polypeptides in any cell-free systems.

BRIEF DESCRIPTION OF THE FIGURES

The invention will further be described with reference to the appended drawings in which.

PREFERABLE VARIANT OF EMBODIMENT OF THE INVENTION

Figure 1:
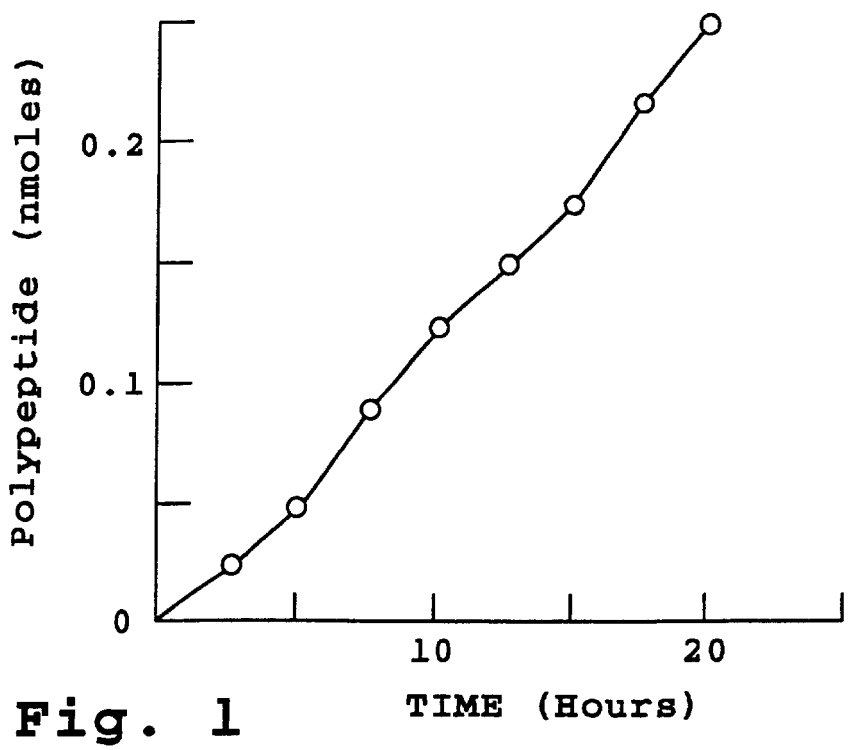
FIG. 1 represents graphic dependencies of the quantity of the synthesized polypeptide in nanomoles on the time of the synthesis in hours.

The technological aspect of the method of preparing polypeptides in cell-free translation systems is simple and the method can be realized as follows.

Extracts of prokaryotic and eukaryotic cells containing ribosomes and all components of the translation machinery but free of endogenous mRNA and DNA are prepared using the known methods. Low molecular weight components including amino acids, ATP, GTP, CTP, UTP, exogenous RNA-polymerase, the gene in the form of a DNA molecule with a promoter site specific to the above polymerase are added to the extract.

The cell-free system is protected from the environment by a porous barrier with pores sufficient to pass specific products. The reaction vessel for the synthesis of polypeptides can be a reservoir in which the cell-free system protected by a porous barrier is placed. A porous barrier can be made either of organic or inorganic material. E.g., ultrafiltration membranes, hollow fibers, microcapsules or films whose shell represents polyelectrolyte complexes can be used as porous barriers. The cell content is then heated to the required temperature.

During the synthesis, the translation products are removed from the reaction vessel through the porous barrier. Simultaneously, substrates from a separate reservoir are supplied into the system to maintain their initial concentration. The specific product withdrawn from the system is concentrated and purified.

The method is illustrated by the following examples:

EXAMPLE 1

1 ml of the reaction mixture contains 350 µl of the S30 extract from E. coli, 0.1 mg of tRNA, 0.04 mg of the DNA fragment containing the gene of the β-lactomase precursor and the promoter for T7 polymerase obtained according to the technique described (Molecular Cloning, 1989, Cold Spring Harbor Laboratory Press, ed. J. Sambrook, E. F. Fritsh, T. Maniatis, p. 1–21), 30,000 U of T7 polymerase, 0.1 mg of pyruvate kinase 50 U of ribonuclease inhibitor from human placenta, 5 µg of each of the protease inhibitors (leupeptin, chymostatin) and α2-macroglobulin in buffer A: 50 mM Tris Ac, pH 7.5, 14 mM $MgCl_2$, 100 mM KAc, 2 mM $CaAc_2$, 1 mM ATP, 0.4 mM GTP, 0.4 mM CTP, 0.4 mM UTP, 10 mM phosphoenolpyruvate, 4 mM dithiothreitol, 50 µM spermidine, 10 µg leukovorin, 40 µM rifampicin, 30 µM [$^3$H]Leu with specific activity 1.7 Cu/mmol and 30 µM each of the other 19 amino acids.

0.5 ml of the cell-free system is placed in a cell for ultra-filtration and the peptide is synthesized at 37° C. The translation products, including the specific product and the products of decomposition, are withdrawn through a porous barrier with a simultaneous delivery of substrates in the form of ATP, GTP, CTP, UTP and amino acids in buffer A during 20 hours. As a result, protein of β-lactomase is obtained. The substrates are supplied at a rate of 2 ml/h.

During the entire synthesis, the specific product is synthesized at a constant rate. The dependence of the amount of the obtained product on the time of synthesis is given in FIG. 1. The abscissa axis shows the time in hours and the ordinate axis shows the amount of the obtained product in nanomoles. As a result, 250 pmol of β-lactomase are synthesized during 20 hours of the system operation.

EXAMPLE 2

1 ml of the reaction mixture contains 350 µl of the S30 extract from E. coli, 0.2 mg of tRNA, 0.1 mg of plasmid containing the gene of dihydrofolate under the promoter of SP6 polymerase obtained according to the technique described (Molecular Cloning, 1989, Cold Spring Harbor Laboratory Press, ed. J. Sambrook, E. F. Fritsh, T. Maniatis, p. 1–21), 20,000 U of SP6 polymerase, 0.1 mg of pyruvate kinase, 50 U of ribonuclease inhibitor from human placenta, 5 µl of each protease inhibitors (leupeptin, chymotrypsin) and α2-macroglobulin in buffer A: 50 mM Tris-Ac, pH 7.5, 14 mM $MgCl_2$, 100 mM KAc, 2 mM $CaAc_2$, 1 mM ATP, 0.4 mM GTP, 0.4 mM CTP, 0.4 mM UTP, 10 mM phosphoenolpyruvate, 4.0 mM dithiothreitol, 50 µM spermidine, 10 µg leukovorin, 40 µM rifampicin, 30 µM [$^{35}$S]Met with specific radioactivity of 800 mCu/mmol and 30 µM of each of the other 19 amino acids.

0.5 ml of the cell-free system is placed in a cell for ultrafiltration and the polypeptide is synthesized-at 37° C. The translation products, including the specific product and the products of decomposition, are removed from the system through a porous barrier with a simultaneous delivery of substrates such as ATP, GTP, CTP, UTP and amino acids in buffer A into the reaction mixture during 20 hours. As a result, protein of dihydrofolate reductase is obtained. The substrates are delivered at a rate of 1.5 ml/h.

Figure 2:
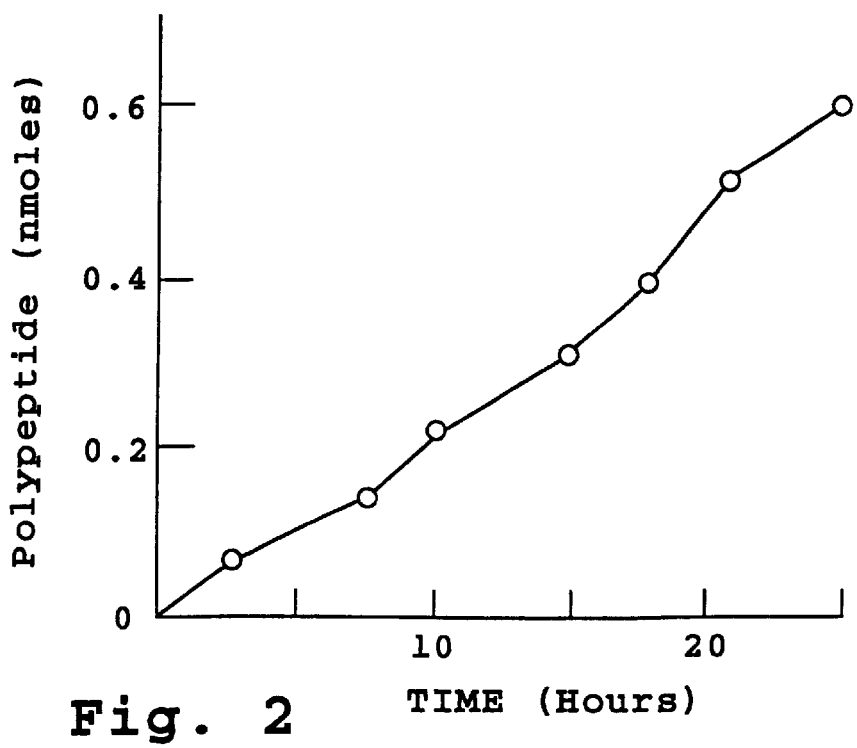
FIG. 2 represents graphic dependencies of the quantity of the synthesized polypeptide in nanomoles on the time of the synthesis in hours.

During the entire synthesis, the specific product is synthesized at a constant rate. The dependence of the amount of the product obtained on the time of the synthesis is given in FIG. 2. The abscissa axis shows the time of the synthesis in hours and the ordinate axis shows the amount of the synthesized product in nanomoles.

As a result, 680 pmol of dihydrofolate reductase are synthesized during 24 hours. The synthesized enzyme is active functionally. Its specific activity was measured as described (Nature, 1960, v. 188, p. 231–232) and was $0.13 \cdot 10^{-4}$ activity units per picomole of the enzyme synthesized.

In this case, the plasmid utilized contains the gene of dihydrofolate reductase under the promoter of SP6 polymerase and the gene of β-lactomose under the promoter of *E. coli* RNA-polymerase. Since rifampicin, an inhibitor of *E. coli* RNA-polymerase, is present in the system, no synthesis of β-lactomase takes place. Therefore, only the specific product is synthesized in the system.

Figure 3:
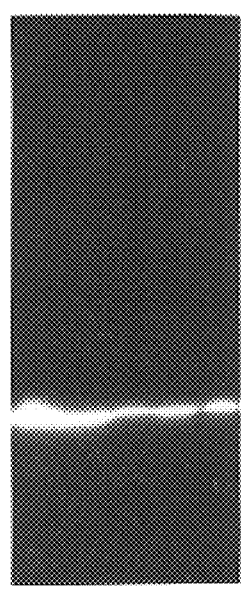
FIG. 3 is a photograph of the fluorogram of SDS-urea-polyacrylamide gel illustrating the distribution of the translation products according to their molecular weight.

The results of the electrophoretic analysis of the polypeptide obtained in 2, 4, 6, 8 and 10 hours after the beginning of the system operation are represented in FIG. 3.

EXAMPLE 3

1 ml of the incubation mixture contains 320 μl of wheat embryo extracts, 0.1 mg of the plasmid with the gene of dihydrofolate reductase under the promoter of SP6 polymerase obtained by the method described (Molecular Cloning, 1989, Cold Spring Harbor Laboratory Press, ed. J. Sambrook, E. F. Fritsh, T. Maniatis, p. 1–21), 20,000 U of SP6 polymerase, 0.1 mg of pyruvate kinase, 50 U of ribonuclease inhibitor from human placenta, 5 μg of each of the protease inhibitors (leupeptin, chymotrypsin) and α2-macroglobulin in buffer A: 40 mM HEPES, pH 7.6, 2.5 mM MgAc$_2$, 70 mM KAc, 1 mM ATP, 0.4 mM GTP, 0.4 mM CTP, 0.4 mM UTP, 0.25 mM spermidine, 4.0 mM dithiothreitol, 6 mM creatin phosphate, 20 μM [$^{14}$C]Leu with specific radioactivity of 21 μCu/mmol, 20 μM of each of the other 19 amino acids.

0.5 ml of the cell-free system is placed in a cell for ultrafiltration and the polypeptide is synthesized at 24° C. The translation products, including the specific product and the products of decomposition, are removed from the system through a porous barrier with a simultaneous delivery of substrates such as ATP, GTP, CTP, UTP and amino acids in buffer A into the reaction mixture during 24 hours. As a result, protein of dihydrofolate reductase is obtained. The substrates are delivered at a rate of 2.0 ml/h.

Figure 4:
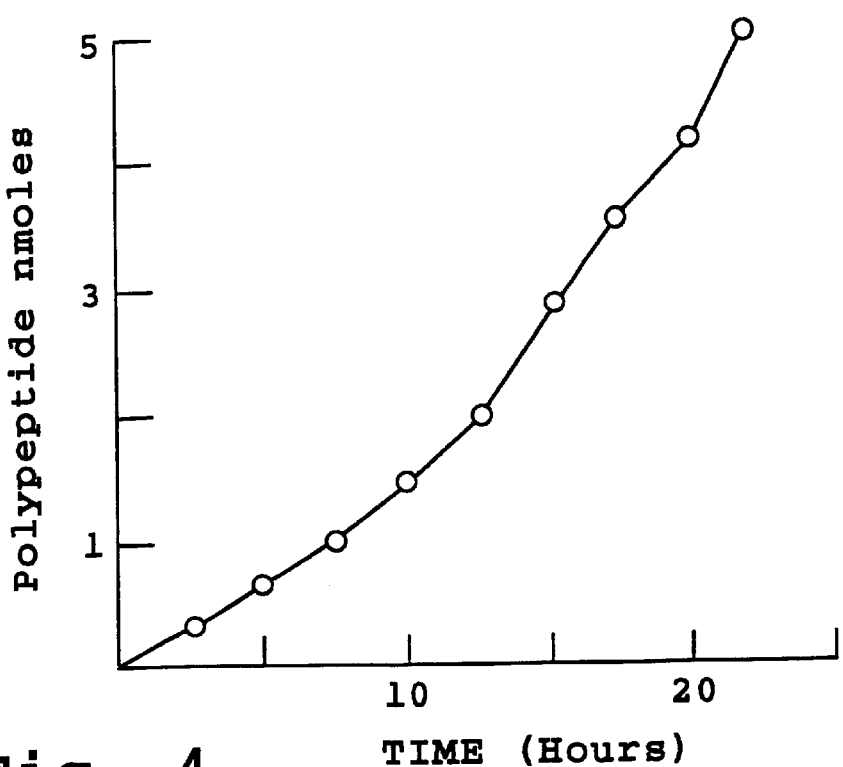
FIG. 4 represents graphic dependencies of the quantity of the synthesized polypeptide in nanomoles on the time of the synthesis in hours.

During the entire synthesis the product is synthesized at a constant rate. The dependence of the amount of the product obtained on the time of the synthesis is given in FIG. 4. The abscissa axis shows the time of the synthesis in hours and the ordinate axis shows the amount of the product obtained in nanomoles. As a result, 5 nmol of dihydrofolate reductase were synthesized. The synthesized enzyme was active functionally. The specific activity of the enzyme obtained was measured as described (Nature, 1960, v. 188, p. 231–232). It was $0.25 \cdot 10^4$ activity units per picomole of the enzyme synthesized.

EXAMPLE 4

1 ml of the incubation mixture contains 600 μl of lysate from rabbit reticulocytes, 0.1 ml of plasmid with the gene of chloramphenicol acetyl transferase under the promoter of SP6 polymerase obtained according to the method described (Molecular Cloning, 1989, Cold Spring Harbor Laboratory Press, ed. J. Sambrook, E. F. Fritsh, T. Maniatis, p. 1–21), 30,000 U of SP6 polymerase, 0.1 mg of pyruvate kinase, 50 U of the ribonuclease inhibitor from human placenta, 5 μg of each of the protease inhibitors (leupeptin, chymotrypsin) and α2-macroglobulin in buffer A: 25 mM HEPES, pH 7.6, 1.5 mM MgAc$_2$, 100 mM KAc, 1 mM ATP, 0.4 mM GTP, 0.4 mM CTP, 0.4 mM UTP, 0.25 mM spermidine, 4.0 mM dithiothreitol, 6 mM creatin phosphate, 20 μM [$^{35}$S]Met with specific radioactivity of 800 mCu/mmol, 20 μM of each of the other 19 amino acids.

0.5 ml of the cell-free system is placed in a cell for ultrafiltration and the polypeptide is synthesized at 37° C. The translation products, including the specified product and the products of decomposition, are removed through a porous barrier with a simultaneous delivery of substrates such as ATP, GTP, CTP, UTP and amino acids in buffer A into the reaction mixture during 34 hours. As a result, a protein of chloramphenicol acetyl transferase is obtained. The substrates are delivered at a rate of 1.5 ml/h.

Figure 6:
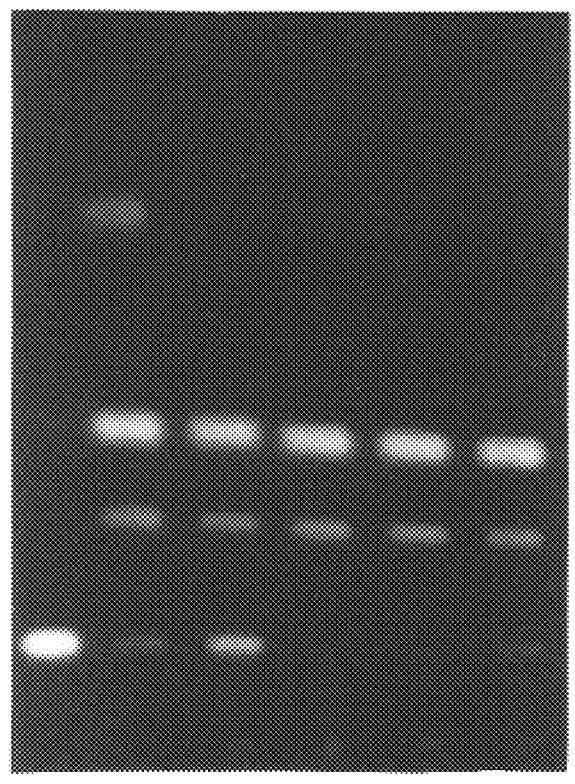
FIG. 6 is a photograph of a thin-layer chromatography radioautograph illustrating the distribution of the products of the reaction catalyzed by chloramphenicol acetyl transferase enzyme (Anal. Biochem., 1987, v. 160, p. 65–67).
Figure 5:
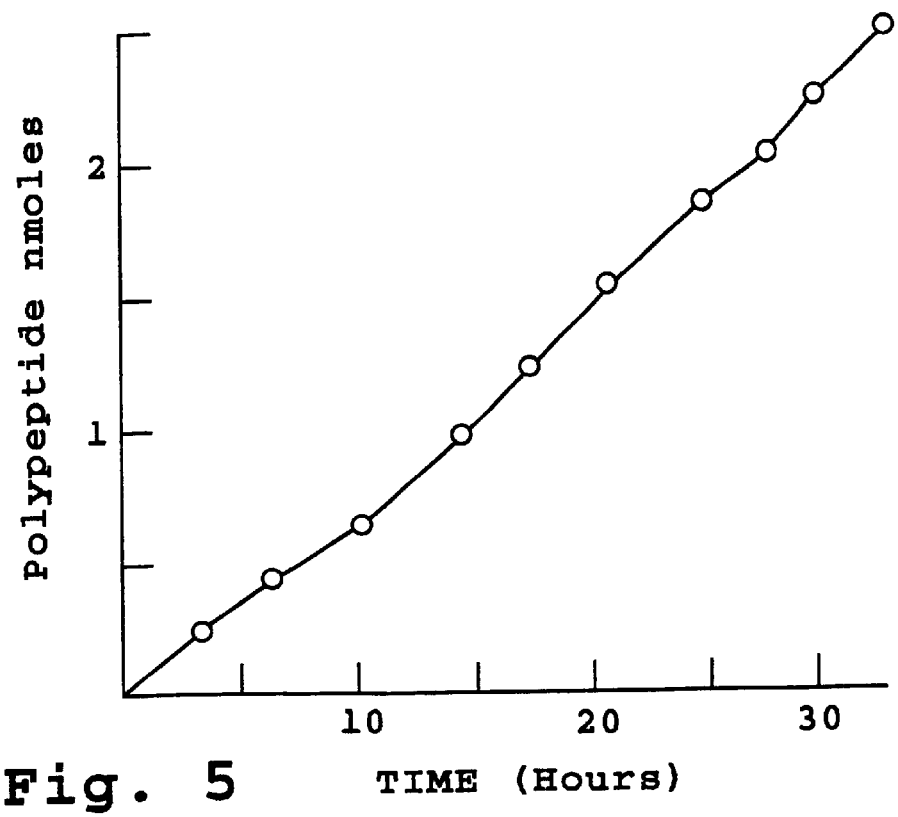
FIG. 5 represents graphic dependencies of the quantity of the synthesized polypeptide in nanomoles on the time of the synthesis in hours.

During the entire synthesis the specific product is synthesized at a constant rate. The dependence of the amount of the product obtained on the time of the synthesis is given in FIG. 5. The abscissa axis shows the time of synthesis in hours and the ordinate axis shows the amount of the product obtained in nanomoles. As a result, 2.5 nmol of chloramphenicol acetyl transferase was synthesized. The enzyme synthesized was active functionally. The functional activity of the enzyme obtained was measured as described (Anal. Biochem., 1987, v. 160, p. 65–67). The results of the analysis of functional activity of the enzyme obtained in 0, 0.5, 5, 7, 9 and 12 hours performed using thin-layer chromatography with a following radioautography are represented in FIG. 6.

EXAMPLE 5

1 ml of the incubation mixture contains 600 μl of lysate from rabbit reticulocytes, 0.1 mg of plasmid with the gene of dihydrofolate reductase under the promoter of SP6 plasmid obtained according to the method described (Molecular Cloning, 1989, Cold Spring Harbor Laboratory Press, ed. J. Sambrook, E. F. Fritsh, T. Maniatis, p. 1–21), 30,000 U of SP6 polymerase, 0.1 mg of pyruvate kinase, 50 U of the ribonuclease inhibitor from human placenta, 5 μg of each of the protease inhibitors (leupeptin, chymotrypsin) and α2-macroglobulin in buffer A: 25 mM HEPES, pH 7.6, 1.5 mM MgAc$_2$, 1 mM ATP, 0.4 mM GTP, 0.4 mM CTP, 0.4 mM UTP, 0.25 mM spermidine, 4.0 mM dithiothreitol, 6 mM creatin phosphate, 20 μM [$^{14}$C]Leu with specific radioactivity of 21 mCu/mmol, 20 μM each of the other 19 amino acids.

0.5 ml of the cell-free system is placed in a cell for ultrafiltration and the polypeptide is synthesized at 37° C. The translation products, including the specific product and the products of decomposition are removed through a porous barrier with a simultaneous delivery of substrates such as ATP, GTP, CTP, UTP and amino acids in buffer A during 20 hours. As a result, a protein of dihydrofolate reductase is obtained. The substrates are delivered with a rate of 2.0 ml/h.

Figure 7:
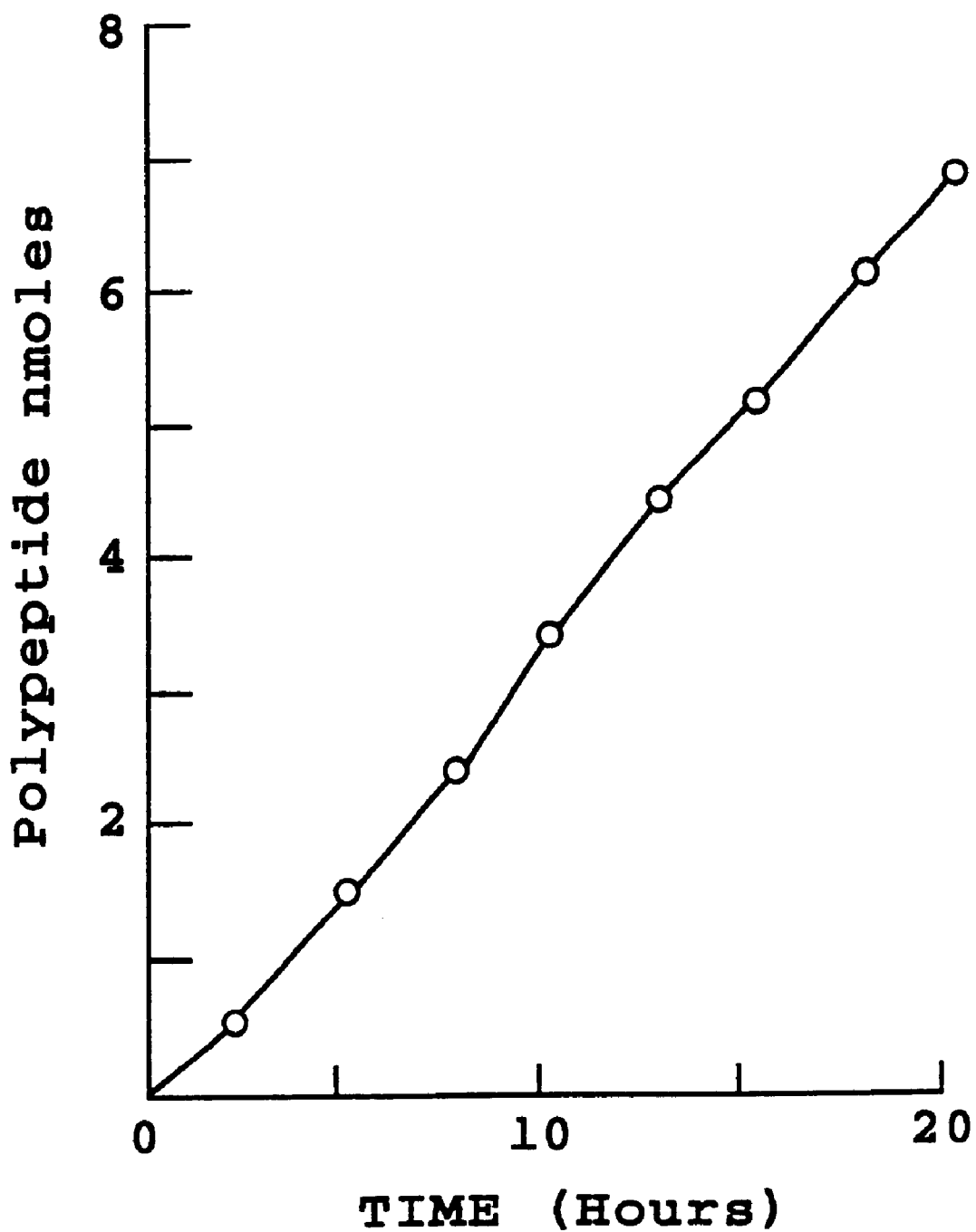
FIG. 7 represents graphic dependencies of the quantity of-the synthesized polypeptide in nanomoles on the time of the synthesis in hours.

During the entire synthesis the product is synthesized at a constant rate. The dependence of the amount of the product obtained on the time of the synthesis is given in FIG. 7. The abscissa axis shows the time of the synthesis in hours and the ordinate axis shows the amount of the product obtained in nonomoles. As a result, 7.0 nmol of dihydrofolate reductase is synthesized. The enzyme synthesized is active functionally. The specific activity of the enzyme obtained measured as described (Nature, 1960, v. 188, p. 231–232) is $0.3 \cdot 10^{-4}$ activity units per picamole of the enzyme synthesized.

Industrial Applicability

The polypeptide obtained according to the invention can be used in medicine, agriculture, and bioelectronics. The method is a multi-purpose one as it ensures synthesis of a template RNA in the process of polypeptide preparation.

What is claimed is:

1. A cell-free method of synthesizing a desired polypeptide, the method comprising:
   (a) adding, to a vessel comprising an ultrafiltration membrane barrier, a mixture comprising: a eukarotic cell extract capable of supporting in vitro translation, an exogenous prokaryotic RNA-polymerase, ATP, GTP, CTP, UTP, amino acids, and a DNA molecule comprising a gene encoding the desired polypeptide under the control of a promoter specific to said exogenous RNA polymerase;
   (b) continuously adding to the vessel the substrates ATP, GTP, CTP, UTP and amino acids, at a rate that maintains their initial concentration in the vessel; and
   (c) continuously removing from the vessel, through the ultra-filtration barrier, the products of the process, including AMP, GDP, CDP, UDP, pyrophosphate, inorganic phosphate, and the desired polypeptide.

2. The method of claim 1, wherein the DNA molecule is produced by amplification of a gene encoding the desired polypeptide.

3. The method of claim 1, wherein the DNA molecule is a plasmid DNA molecule.

4. The method of claim 1, wherein the exogenous RNA-polymerase is an exogenous phage RNA-polymerase.

5. The method of claim 4, wherein the exogenous phage RNA-polymerase is SP6 RNA-polymerase.

6. The method of claim 4, wherein the exogenous phage RNA-polymerase is T7 RNA-polymerase.

7. The method of claim 1, wherein the eukaryotic cell extract is a plant cell extract.

8. The method of claim 7, wherein the plant cell extract is a wheat embryo extract.

9. The method of claim 1, wherein the eukaryotic cell extract is an animal cell extract.

10. The method of claim 9, wherein the animal cell extract is a rabbit reticulocyte lysate.

* * * * *